(12) United States Patent
Gorantla et al.

(10) Patent No.: US 8,344,159 B2
(45) Date of Patent: Jan. 1, 2013

(54) CARVEDILOL PHOSPHATE SESQUIHYDRATE

(75) Inventors: Seeta Ramanjaneyulu Gorantla, Hyerabad (IN); Mohan Bandari, Hyerabad (IN); Nageshwara Rao Karusala, Hyerabad (IN); Sankara Sastry Tummalapalli Uma, Hyerabad (IN)

(73) Assignee: Mylan Laboratories Limited, Hyderabad (IN)

( * ) Notice: Subject to any disclaimer, the term of this patent is extended or adjusted under 35 U.S.C. 154(b) by 281 days.

(21) Appl. No.: 12/304,645

(22) PCT Filed: Jun. 11, 2007

(86) PCT No.: PCT/IN2007/000232
§ 371 (c)(1),
(2), (4) Date: Dec. 12, 2008

(87) PCT Pub. No.: WO2007/144900
PCT Pub. Date: Dec. 21, 2007

(65) Prior Publication Data
US 2009/0259051 A1 Oct. 15, 2009

(30) Foreign Application Priority Data
Jun. 14, 2006 (IN) .......................... 1028/CHE/2006

(51) Int. Cl.
*C07D 209/88* (2006.01)
(52) U.S. Cl. ...................................... 548/444
(58) Field of Classification Search .................. None
See application file for complete search history.

(56) References Cited

U.S. PATENT DOCUMENTS
8,124,644 B2   2/2012   Levi

FOREIGN PATENT DOCUMENTS
WO   WO-2004/002419   1/2004
WO   WO 2005/051322 *  6/2005

OTHER PUBLICATIONS

Brittain, H.G., Polymorphism in Pharmaceutical Solids—Drugs and the Pharmaceutical Sciences, V. 95; New York Marcel Dekker, Inc., 1999, relevant pages attached.*
Jain et al., Indian Drugs, 1986, 23 (6).*
Rodriguez-Spong et al. Advanced Drug Delivery Reviews, 56 (2004), pp. 241-274.*
Rouhi, Chemical & Engineering News, Feb. 24, 2003, pp. 33-34.*
Ulicky, "amorphous substance," Comprehensive Dictionary of Physical Chemistry, NY: Prentice Hall, 1992, p. 21.*
Berge et al. "Pharmaceutical Salts". Journal of Pharmaceutical Sciences. Jan. 1977, vol. 66, No. 1, pp. 1-19.
Haynes et al. "Occurrence of Pharmaceutically Acceptable Anions and Cations in the Cambridge Structural Database." Journal of Pharmaceutical Sciences, vol. 94, No. 10, pp. 2111-2120, (2005).

* cited by examiner

*Primary Examiner* — Joseph K. McKane
*Assistant Examiner* — Alicia L Otton
(74) *Attorney, Agent, or Firm* — Ladas & Parry LLP

(57) ABSTRACT

The present invention relates a novel crystalline 1-(Carbazol-4-yloxy-3-[[2-(o-methoxyphenoxy)ethyl]amino]-2-propanol phosphate sesquihydrate (Carvedilol dihydrogenphosphate sesquihydrate), methods of preparing the sesquihydrate by adding phosphoric acid to a suspension of Carvedilol in water, water miscible solvents or a mixture of water and water miscible organic solvent followed by isolating the product directly or by adding solvent.

2 Claims, 3 Drawing Sheets

CARVEDILOL PHOSPHATE SESQUIHYDRATE

BACKGROUND OF THE INVENTION

1. Field of the Invention

The present invention relates to new crystalline forms of carvedilol and pharmaceutical compositions thereof, as well as processes for its preparation and manufacture.

2. Description of the Related Art

Carvedilol, 1-(Carbazol-4-yloxy-3-[[2-(o-methoxyphenoxy)ethyl]amino]-2-propanol (CAS Registry No. 72956-09-3), has the formula as given below:

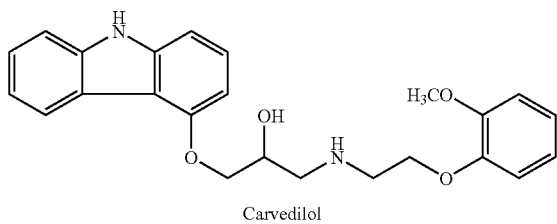 [SMILES: COc1ccccc1OCCNCC(O)COc1cccc2[nH]c3ccccc3c12]

Carvedilol

Carvedilol as a free base is used for treatment of hypertension, congestive heart failure and angina. The currently commercially available carvedilol product is a conventional, tablet prescribed as a twice-a-day medication.

U.S. Pat. No. 4,503,067 discloses carbazolyl-(4)-oxypropanolamine compounds and salts thereof with pharmacologically acceptable acids. The patent discloses the conversion of carbazolyl-(4)-oxypropanolamine compounds into their pharmacologically acceptable salts, by reacting with an equivalent amount of an inorganic or organic acid such as hydrochloric acid, hydrobromic acid, phosphoric acid, sulphuric acid, acetic acid, citric acid, maleic acid or benzoic acid in an organic solvent.

International Application publication number WO 2004/002419 discloses and designates the following forms of carvedilol, pharmaceutical compositions thereof and methods of using the same to treat cardiovascular diseases including hypertension, congestive heart failure and angina:

| | |
|---|---|
| Carvedilol dihydrogen phosphate hemihydrate | Form-I |
| Carvedilol dihydrogen phosphate dihydrate | Form-II |
| Carvedilol dihydrogen phosphate methanol solvate | Form-III |
| Carvedilol dihydrogen phosphate dihydrate | Form-IV |
| Carvedilol dihydrogen phosphate | Form-V |
| Carvedilol hydrogen phosphate | Form-VI |

The WO 2004/002419 application further characterizes (XRD, thermal analysis, FT-Raman spectrums) crystalline forms of carvedilol phosphate salt. The processes disclosed for preparation of carvedilol dihydrogen phosphate hemihydrate (Form-I) involve the addition of phosphoric acid to the solution of carvedilol in acetone-water, followed by isolation and drying under vacuum. The processes disclosed for preparation of carvedilol dihydrogen phosphate dihydrate involve the slurrying of the Form-I with an acetone/water mixture between 10 and 30° C. for several days, and for the preparation of carvedilol dihydrogen phosphate methanol solvate (Form-III) by slurring Form-I in methanol between 10 and 30° C. for several days. The application further discloses that the carvedilol dihydrogen phosphate displays higher solubility when compared to the free base of carvedilol.

International Application publication number WO 2005/051383 discloses several crystalline carvedilol salts selected from mandelate, lactate, maleate, sulfate, glutarate, mesylate, phosphate, citrate, hydrobromide, oxalate, hydrochloride, benzoate as solvates and anhydrous forms. The application further discloses pharmaceutical compositions containing the above salts, anhydrous forms or solvates thereof, and methods of using the compound in the treatment of certain disease in mammals.

It has now been shown that a novel crystalline form of carvedilol phosphate (i.e., carvedilol dihydrogen phosphate salt) can be isolated as pure crystalline, sesquihydrate, which is found to be more stable.

SUMMARY AND OBJECTS OF THE INVENTION

It is a principle object of the present invention to provide a novel crystalline form of carvedilol as carvedilol dihydrogen phosphate sesquihydrate.

It is another object of the present invention to provide a method for preparing crystalline carvedilol dihydrogen phosphate sesquihydrate.

It is still another object of the present invention to provide a preparation containing stable crystalline carvedilol dihydrogen phosphate sesquihydrate.

Briefly described, those and other objects and advantages of the present invention are accomplished, as embodied and fully described herein, by crystalline carvedilol dihydrogen phosphate sesquihydrate having the formula:

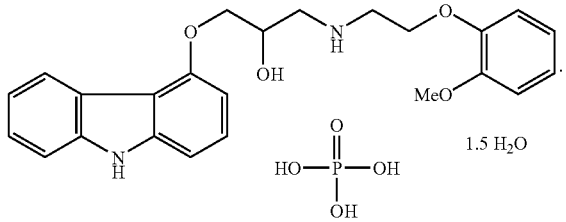 [SMILES: COc1ccccc1OCCNCC(O)COc1cccc2[nH]c3ccccc3c12 ; O=P(O)(O)O]

The carvedilol is characterized by an x-ray powder diffraction pattern having peaks at about 5.83 (±) 0.2, 6.46 (±) 0.2, 6.78 (±) 0.2, 14.39 (±) 0.2, 15.11 (±) 0.2, 16.21 (±) 0.2, 17.26 (±) 0.2, 18.00 (±) 0.2, 19.01 (±) 0.2, 20.46 (±) 0.2, 20.97 (±) 0.2, 21.81 (±) 0.2, 24.45 (±) 0.2, and 26.11 (±) 0.2 two-theta. The carvedilol is also characterized by a differential scanning calorimetry thermogram having a peak at about 105° C. to about 120° C. and 156° C. (±) 0.1%, and by a water content of between about 4.0 to 7.0% w/w. The aforementioned objects and advantages of the present invention are also accomplished, as embodied and fully described herein, by a process for preparing carvedilol dihydrogen phosphate sesquihydrate by suspending carvedilol in one of water, water miscible solvents, and a mixture of water and water miscible organic solvents; reacting the suspension with phosphoric acid to form a solution; adding a solvent to the solution; and isolating the product. The water miscible organic solvent may be ethanol, n-propyl alcohol, isopropyl alcohol, acetone, acetonitrile, dioxane, tetrahydrofuran, ethyl acetate, isopropyl acetate, dimethoxy ethane and mixtures thereof. The solvent may be water, ethanol, n-propyl alcohol, isopropyl alcohol, acetone, acetonitrile, dioxane, tetrahydrofuran, ethyl acetate, isopropyl acetate, dimethoxy ethane and mixtures thereof.

DETAILED DESCRIPTION OF THE PREFERRED EMBODIMENTS

Figure 1:
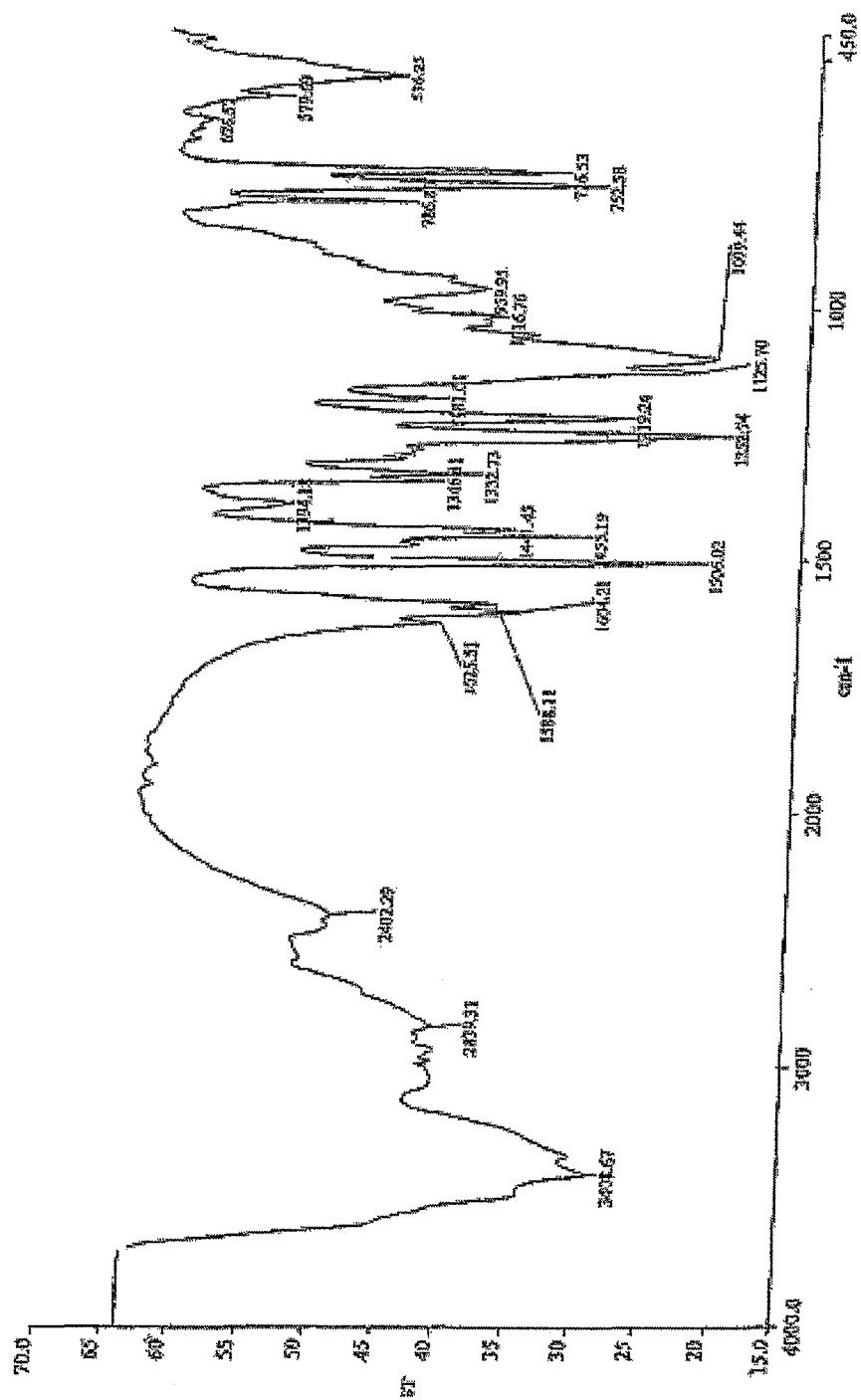
FIG. 1 is an FT-IR spectrum for carvedilol phosphate sesquihydrate according to a preferred embodiment of the present invention.

Several preferred embodiments of the present invention are described for illustrative purposes, it being understood that the invention may be embodied in other forms not specifically shown in the drawings.

Thus, in accordance with the present invention, a novel crystalline carvedilol dihydrogen phosphate sesquihydrate and process for preparing the carvedilol phosphate sesquihydrate is provided.

The novel crystalline carvedilol dihydrogen phosphate sesquihydrate according to the present invention is the compound of formula (I):

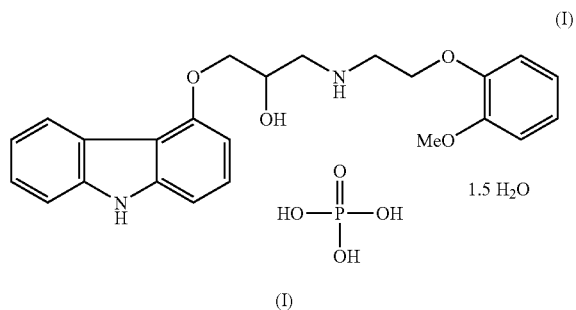 [SMILES: COc1ccccc1OCCNCC(O)COc1cccc2[nH]c3ccccc3c12 ; O=P(O)(O)O ; "(I)"]

(I)

Figure 2:
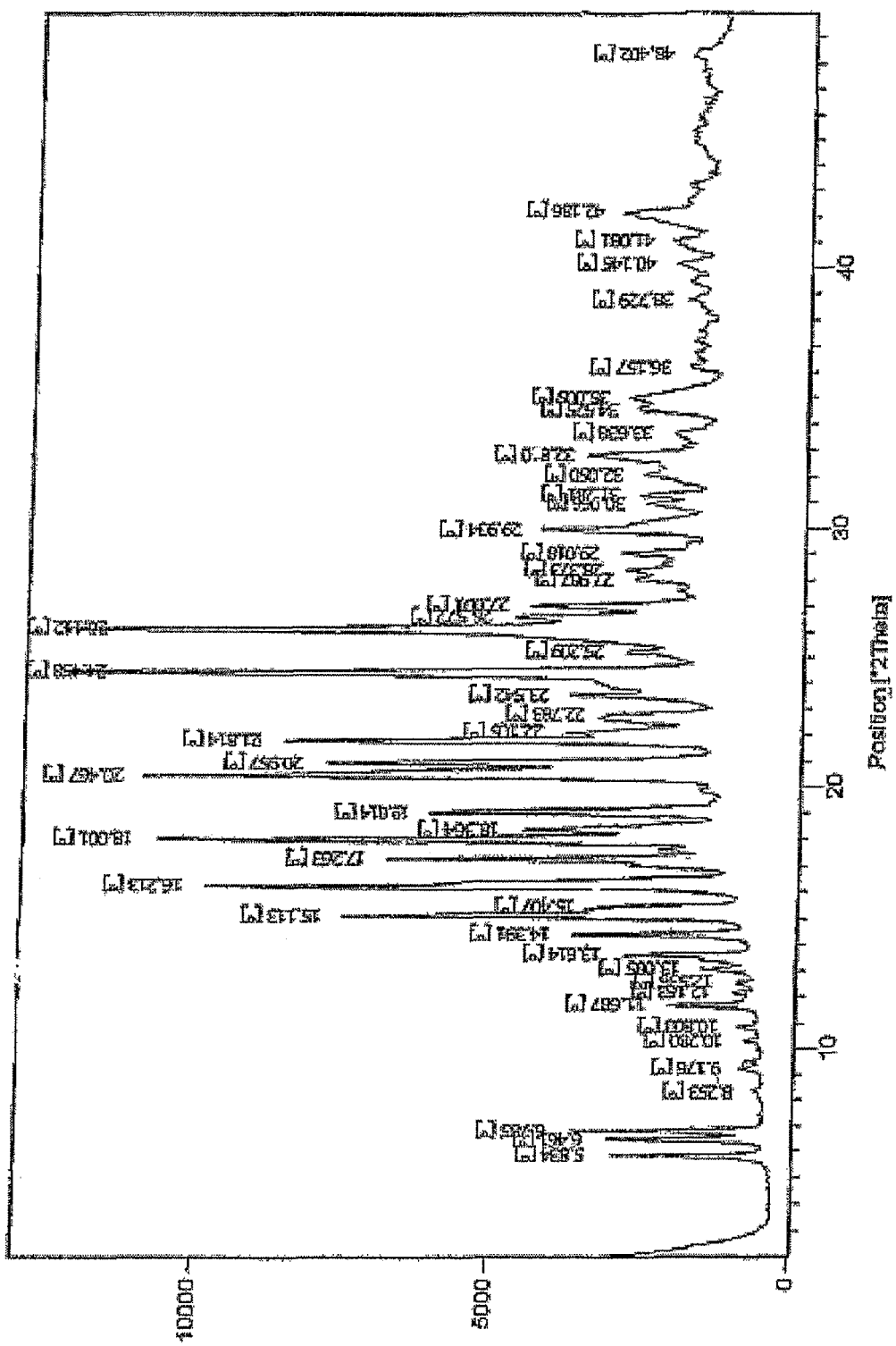
FIG. 2 is and X-ray powder diffractogram for the carvedilol phosphate sesquihydrate of FIG. 1
Figure 3:
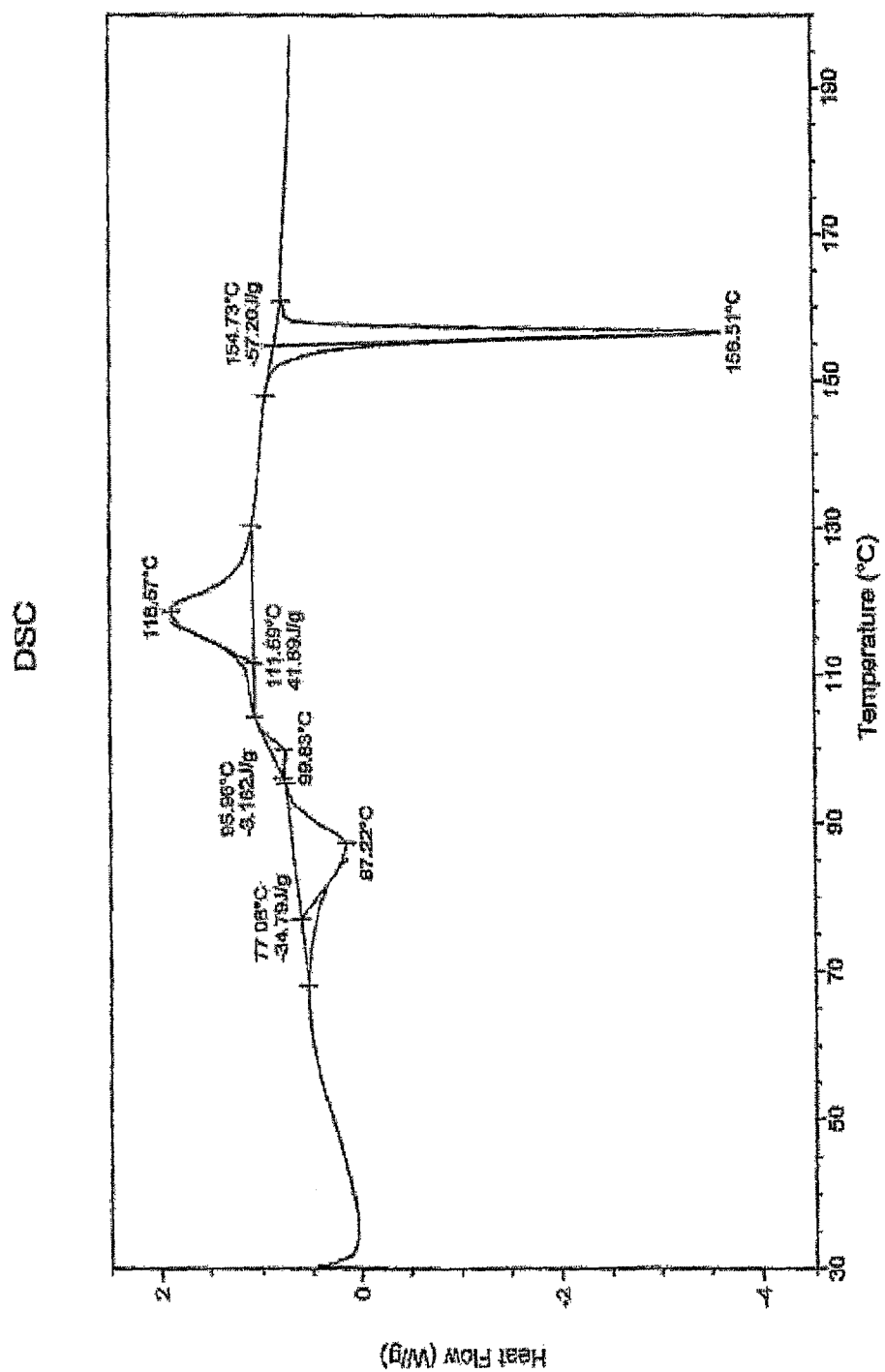
FIG. 3 is a DSC curve for the carvedilol phosphate sesquihydrate of FIG. 1.

According to the present invention, the compound of formula (I) is characterized by an x-ray diffraction pattern as shown in FIG. 2, which shows characteristic peak two-theta (θ) values at about 5.83, 6.46, 6.78, 14.39, 15.113, 16.21, 17.26, 18.00, 19.01, 20.46, 20.97, 21.81, 24.45 and 26.11 (±) 0.2 two-theta. It may also be characterized by a differential scanning calorimetry (DSC) thermogram as shown in FIG. 3, which shows peaks at about 105° C. to about 120° C. and 156° C. (±) 1° C. It may also be characterized by having a moisture content ranging between about 4.0 to 7.0%, with a preferred moisture content ranging between about 4.5 to 6.0%. The theoretical moisture content requirement for carvedilol dihydrogen phosphate sesquihydrate is 5.08%.

The DSC thermogram shown in FIG. 3 includes four characteristic peaks. The first two peaks are endothermal peaks at an extrapolated onset temperature ranging from 65 to 100° C., which is attributed to a two step release of water. The third peak is an exothermic peak at an extrapolated onset temperature ranging from 100 to 125° C., which corresponds to the transition from hydrated phase to an anhydrous phase which is identified with a peak at 114±1° C. The fourth peak is an endothermal peak at an extrapolated onset temperature of 156±1° C., which corresponds to the complete melting of the product.

One process for preparing crystalline Carvedilol phosphate sesquihydrate according to the present invention includes the steps of: (1) suspending the carvedilol in water, water miscible solvents, or a mixture of water and water miscible organic solvents, (2) reacting the suspension with phosphoric acid, (3) adding a solvent, and (4) isolating the carvedilol product.

Another process for preparing crystalline carvedilol dihydrogen phosphate sesquihydrate according to the present invention includes first suspending carvedilol in water or in a water miscible organic solvent selected from ethanol, n-propyl alcohol, isopropyl alcohol, acetonitrile, dioxane, tetrahydrofuran, ethyl acetate, isopropyl acetate, dimethoxy ethane and mixtures thereof. The preferred water miscible organic solvent is isopropyl alcohol and ethanol.

Next, to the suspension is added phosphoric acid at a temperature between 0 and 45° C., preferably at a temperature of between about 25 to 35° C., wherein the concentration of phosphoric acid is between about 5% to 85% weight/weight. Following addition of the phosphoric acid, the reaction mass is maintained at a temperature between about 0 to 45° C., preferably at a temperature between about 25 to 35° C., for about 30 min to 4 hrs.

Next, a solvent is then added to the above reaction mass, wherein the solvent is selected from water, ethanol, n-propyl alcohol, isopropyl alcohol, acetone, acetonitrile, dioxane, tetrahydrofuran, ethyl acetate, isopropyl acetate, dimethoxy ethane and mixtures thereof. The preferred solvent is acetone or ethanol.

The reaction mass is then maintained for about 1 to 5 hrs. at a temperature between about 20 to 40° C., preferably at a temperature between about 25 to 35° C. Optionally, the reaction mass is maintained without adding a solvent.

Finally, the product is isolated at a temperature between about 0 and 5° C., and dried at a temperature between about 40 to 45° C.

The carvedilol dihydrogen phosphate sesquihydrate according to the present invention is further characterized by $^1$H NMR (300 MHz, DMSO, ppm): 11.3 (s, 1H), 8.25-6.6 (m, 10H), 4.32-4.15 (m, 5H), 3.7 (s, 3H), 3.2-3.08 (m, 4H).

Advantages of the carvedilol dihydrogen phosphate sesquihydrate having the aforementioned characteristics and made in accordance with the procedures described above include the following:

1. Better solubility as compared to carvedilol base, so it increases bio availability;

2. More stable as compared to carvedilol base, so the color of the final product is superior.

3. The quality of the carvedilol phosphate is better than carvedilol.

The invention is further illustrated with a few non-limiting examples as follows.

EXAMPLE 1

Preparation of Carvedilol Phosphate Sesquihydrate

Carvedilol (25.0 gm) was suspended in DM water (100.0 ml), and to the suspension phosphoric acid (7.80 g of 85% phosphoric acid in 50 ml of water) was added slowly at 25-35° C. over 2 hrs. The reaction mass was maintained for 30 min. at 25-35° C. To the reaction mass, 125 ml of acetone was slowly charged in 1 hr at 25-35° C. and maintained for 4 hrs at 25-35° C. The suspension was cooled to 0-5° C. and maintained for 2 hr at 0-5° C. The product was filtered, washed with chilled acetone (50.0 ml) and dried at 40-45° C., which yielded carvedilol phosphate sesquihydrate. Output: 24.0 g. Purity by HPLC: 99.87%

EXAMPLE 2

Preparation of Carvedilol Phosphate Sesquihydrate

Carvedilol (25 gm) was suspended in DM water (100 ml), and to the suspension phosphoric acid (7.80 g of 85% phosphoric acid in 50 ml of water) was added slowly at 25-35° C. The reaction mass was maintained for 4 hrs at 25-35° C. To the reaction mass, 125 ml of ethanol was slowly charged in 1 hr at 25-35° C. and maintained for 4 hrs at 25-35° C. The suspension was cooled to 0-5° C. and maintained for 2 hr at 0-5° C. the product was filtered, washed with chilled ethanol (50.0 ml) and dried at 40-450° C., which yielded carvedilol phosphate sesquihydrate. Output: 24.5 g. Purity by HPLC: 99.85%

EXAMPLE 3

Preparation of Carvedilol Phosphate Sesquihydrate

Carvedilol (25 gm) was suspended in a mixture of IPA (250 ml) and water (25 ml), and to the suspension phosphoric acid (7.80 g of 85% phosphoric acid in 50 ml of water) was slowly added at 25-35° C. over 2 hrs. The reaction mass was maintained for 4 hrs at 25-35° C., and then cooled to 0-5° C. and maintained for 2 hr at 0-5° C. The product was filtered, washed with chilled IPA (50.0 ml), and dried at 40-45° C., which yielded carvedilol phosphate sesquihydrate. Output: 24.0 g. Purity by HPLC: 99.65%

EXAMPLE 4

Preparation of Carvedilol Phosphate Sesquihydrate

Carvedilol phosphate (25 gm) was suspended in a mixture of IPA (250 ml) and water (25 ml), and to the suspension phosphoric acid (7.80 g of 85% phosphoric acid in 50 ml of water) was slowly added at 25-35° C. over 2 hrs. The reaction mass was maintained for 4 hrs at 25-35° C., and then cooled to 0-5° C. and maintained for 2 hr at 0-5° C. The product was filtered, washed with chilled IPA (50.0 ml) and dried at 40-45° C., which yielded carvedilol phosphate sesquihydrate. Output: 24.0 g. Purity by HPLC: 99.65%.

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

We claim:

1. Carvedilol dihydrogen phosphate sesquihydrate having the formula

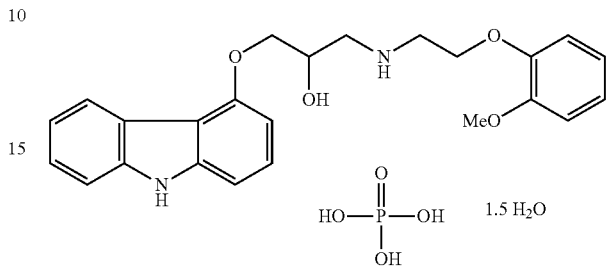

characterized by an x-ray powder diffraction pattern, obtained using Cu/K alpha radiation, having peaks at about 5.83 (±) 0.2, 15.11 (±) 0.2, 16.21 (±) 0.2, 18.00 (±) 0.2, 21.81 (±) 0.2 and 26.11 (±) 0.2 two-theta.

2. Carvedilol dihydrogen phosphate sesquihydrate having the formula

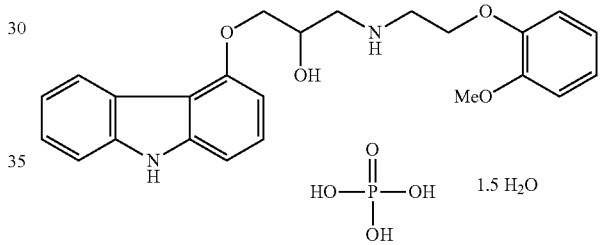

characterized by an x-ray powder diffraction pattern, obtained using Cu/K alpha radiation, having peaks at about 5.83 (±) 0.2, 6.46 (±) 0.2, 6.78 (±) 0.2, 14.39 (±) 0.2, 15.11 (±) 0.2, 16.21 (±) 0.2, 17.26 (±) 0.2, 18.00 (±) 0.2, 19.01 (±) 0.2, 20.46 (±) 0.2, 20.97 (±) 0.2, 21.81 (±) 0.2, 24.45 (±) 0.2, and 26.11 (±) 0.2 two-theta.

* * * * *